United States Patent [19]

Mattox

[11] Patent Number: 5,108,500

[45] Date of Patent: Apr. 28, 1992

[54] STABILIZATION OF WATER INSOLUBLE 3-ISOTHIAZOLONES

[75] Inventor: John R. Mattox, Perkasie, Pa.

[73] Assignee: Rohm and Haas Company, Philadelphia, Pa.

[21] Appl. No.: 625,269

[22] Filed: Dec. 10, 1990

[51] Int. Cl.⁵ .......................... C09D 5/14; C09D 5/16
[52] U.S. Cl. ...................... 106/18.33; 106/2
[58] Field of Search ............. 106/18.32, 18.33

[56] References Cited

U.S. PATENT DOCUMENTS

| | | | |
|---|---|---|---|
| 3,523,121 | 8/1970 | Lewis et al. | 260/306.7 |
| 3,761,488 | 9/1973 | Lewis et al. | 260/302 |
| 3,870,795 | 3/1975 | Miller et al. | 424/270 |
| 4,067,878 | 1/1978 | Miller et al. | 260/302 A |
| 4,105,431 | 8/1978 | Lewis et al. | 106/18.32 |
| 4,129,448 | 12/1978 | Greenfield et al. | 106/15 R |
| 4,150,026 | 4/1979 | Miller et al. | 260/299 |
| 4,165,318 | 8/1979 | Greenfield et al. | 260/302 A |
| 4,241,214 | 12/1980 | Miller et al. | 548/101 |
| 4,608,183 | 8/1986 | Rossmore | 252/36 |
| 4,783,221 | 11/1988 | Grove | 106/18.22 |
| 4,898,895 | 2/1990 | Masuoka et al. | 523/122 |

*Primary Examiner*—William R. Dixon, Jr.
*Attorney, Agent, or Firm*—Michael B. Fein

[57] ABSTRACT

An isothiazolone concentrate composition comprising an oil soluble, water insoluble 3-isothiazolone compound and an amount sufficient to stabilize said 3-isothiazolone compound in a subsequent use dilution of a copper salt selected from the group consisting of copper dodecylbenzene sulfonate, copper dioctyl sulfosuccinate, and copper petroleum sulfonate and a sufficient amount of an organic solvent to dissolve said 3-isothiazolone and said copper salt.

13 Claims, No Drawings

STABILIZATION OF WATER INSOLUBLE 3-ISOTHIAZOLONES

BACKGROUND OF THE INVENTION

1. Field of the Invention

This invention relates to stabilization of water insoluble 3-isothiazolones.

2. Description of the Prior Art

Isothiazolones are well known mildewcides for film forming compositions. Isothiazolones are generally unstable without the addition of a stabilizer. In aqueous paint formulations, copper nitrate is a well known stabilizer for isothiazolones.

U.S. Pat. Nos. 3,870,795 and 4,067,878 teach the stabilization of isothiazolones against chemical decomposition by addition of a metal nitrate or metal nitrate salts, but teach that other common metal salts, including carbonates, sulfates, chlorates, perchlorates, and chlorides are ineffective in stabilizing solutions of isothiazolones, such solutions usually being in water or in an hydroxylic solvent and immiscible with solvent-soluble isothiazolones. Salts of organic carboxylic acids of more than six carbon atoms with copper are not taught or considered in these patents.

U.S. Pat. Nos. 4,150,026 and 4,241,214 teach metal salt complexes of isothiazolones useful because of their enhanced thermal stability, while retaining biological activty. The metal salts listed do not include salts of organic carboxylic acids of more than six carbon atoms with copper, or complexes of copper with organic-soluble reagents.

U.S. Pat. No. 4,608,183 teaches synergistic biocidal mixture of isothiazolones and a metal complex with a polyfunctional ligand, requiring that the metal complex itself be a biocide. Illustrated specifically is a water-soluble cupric disodium citrate. It is known to use certain organic stabilizers for isothiazolones, generally for use situations where metal salts may create problems, such as corrosion, coagulation of latices, insolubility in non-aqueous media, interaction with the substrate to be stabilized, and the like. Formaldehyde or formaldehyde-releasing chemicals are known stabilizers, (see U.S. Pat. Nos. 4,165,318 and 4,129,448).

Pending patent application serial no. 377,984 discloses stabilization of water insoluble isothiazolones with water insoluble copper compounds which are copper salts of organic carboxylic acids.

In certain applications it is desirable to avoid addition of organic stabilizers by virtue of their volatility, decomposition under high heat, higher cost, difficulty in handling, potential toxicity, and the like. Formaldehyde is a suspected carcinogen, and it is desirable not to use formaldehyde or formaldehyde releasing chemicals in applications where contact with human skin or lungs may occur.

In actual use, copper salts of inorganic acids, such as copper (II) sulfate or nitrate, have proved efficacious in stabilization of isothiazolones. However, water-soluble inorganic copper salts are undesirable in effluent streams in such operations as in the manufacture of stabilized isothiazolones or in their blending into a product or the use of that product. Such water-soluble copper salts, especially the chlorides, may contribute to possible corrosion, or in the presence of polymers in aqueous dispersion may lead to coagulation of the dispersion. The water-soluble salts may not be readily miscible with certain of the water-insoluble isothiazolones, leading to separation and lowering of stability of a stabilizer concentrate.

Grove, U.S. Pat. No. 4,783,221 shows metal salts of organic carboxylic acids containing at least 6 carbon atoms wherein the metal is selected from the group consisting of copper and other transition metals, zinc, antimony, and lead, with an isothiazolone compound, and a solvent/diluent to preserve wood.

SUMMARY OF THE INVENTION

It is therefore an object of the present invention to provide a mildew-resistant paint composition which avoids the problems of previous metal salt stabilizers.

These objects, and others as will become apparent from the following description, are achieved by the present invention which comprises an isothiazolone concentrate composition comprising a. an oil soluble, water insoluble 3-isothiazolone compound of the formula:

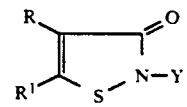

wherein Y is an unsubstituted alkyl group of 2 to 18 carbon atoms; a substituted alkyl group of 2 to 18 carbon atoms having at least one hydrogen atom replaced by hydroxy, halo, cyano, alkylamino, dialkylamino, phenylamino, halophenylamino, carboxy, carbalkoxy, alkoxy, aryloxy, morpholino, piperidino, pyrrolidonyl, carbamoxy, or isothiazolonyl, wherein the total number of carbon atoms in the substituted alkyl group does not exceed 18; an unsubstituted or halo-substituted alkenyl group of 4 to 18 carbon atoms; unsubstituted or halo-substituted alkynyl group of to 18 carbon atoms; an unsubstituted or alkyl-substituted cycloalkyl group having a four to six carbon atom ring and up to 12 carbon atoms; an unsubstituted or a halo-, lower alkyl-, or lower alkoxy-substituted aralkyl group wherein the total number of carbon atoms in the aralkyl group does not exceed 10; or an unsubstituted or a halo-, nitro-, lower alkyl-, or lower carbalkoxy-, substituted aryl group wherein the total number of carbon atoms in the aryl group does not exceed 10; and R and R$^1$ are the same or different substituent selected from hydrogen, halogen, or a (C$_1$-C$_4$) alkyl group;

One skilled in this art would recognize that the water solubility of the isothiazolones depends on the type of substituent (i.e. R, R$^1$ and Y). For example, the carbon content of the alkyl group will vary depending on the R or R$^1$ or both the R and R$^1$ substituent. As further illustration of what is meant is that, for example, when R=R$^1$=halo, the alkyl group can be as low as two carbon atoms and the water solubility will be less than 1%. When only one of the R or R$^1$ is halo and the other hydrogen, the alkyl group will be at least four carbon atoms. When both R and R$^1$ is hydrogen then the alkyl group must be at least six carbon atoms.

b. an amount sufficient to stabilize said 3-isothiazolone compound in a subsequent use dilution of a copper salt selected from the group consisting of copper dodecylbenzene sulfonate, copper dioctyl sulfosuccinate, and copper petroleum sulfonate and;

c. a sufficient amount of an organic solvent to dissolve said 3-isothiazolone and said copper salt.

In another aspect, the invention comprises a method of imparting mildew resistance to a coating, comprising impregnant, marine antifoulant, metal working composition, wood and the like using the aforementioned composition.

DETAILED DESCRIPTION OF THE INVENTION AND THE PREFERRED EMBODIMENTS

The isothiazolones useful in the invention are well known and are described in U.S. Pat. No. 3,523,121 and 3,761,488. Highly preferred isothiazolones are 2-octyl-3-isothiazolone and 4,5-dichloro-2-octyl-3-isothiazolone.

The oil soluble copper compounds useful in the invention are copper dodecylbenzene sulfonate, copper dioctyl sulfosuccinate, and copper petroleum sulfonate.

Solvents may be used to dissolve the isothiazolones and may be any organic solvent which is miscible with the isothiazolones, is compatible with the proposed end use, does not destabilize the isothiazolone, and does not react with the copper salt to eliminate its stabilizing action.

Hydroxylic solvents, for example, polyols, such as glycols, monoethers of glycols, alcohols, and the like, may be used. An hydroxylic coalescent, such as Texanol (trimethyl-1,3-pentanediol monoisobutyrate) also may be used. In certain formulations, hydrocarbons, either aliphatic or aromatic, are useful solvents. Typical solvents are dipropylene glycol, dipropylene glycol monoethyl ether, xylene, mineral spirits, and the like. Solvents may be used in admixture as long as the copper salt remains soluble or is well dispersed enough so as to be added conveniently and uniformity to the test formulation.

The amounts of copper salt employed will vary depending on use conditions and concentrations of the isothiazolone in the mixture. Generally, when solvent is present, from about 0.01 to about 50 parts of said isothiazolone (a); from about 0.0001 to about 10 parts of said copper compound (b), and which further comprises from about 40 to about 99.9899 parts of a solvent can be used. Preferably, ratios of from 1 to 25 parts of (a), from 0.1 to 10 parts of (b) and from 65 to 98.9 parts of the solvent are suitable. In more concentrated solutions, effective amounts of copper salt based on isothiazolone are in the ratios of from about 1:50 to about 2:1. Obviously higher amounts may be used, but at additional cost. At high levels of dilution of this isothiazolone (such as from 1 to 2 percent isothiazolone in the solvent), the ratio of stabilizer to isothiazolone can range from about 1:10 to about 3:1.

Other salt stabilizers such as those described in U.S. Pat. Nos. 3,870,795; 4,067,878; 4,150,026 and 4,241,214 can also be included.

Because the preferred isothiazolones and the stabilizers of the present invention are both organic-soluble and water-insoluble, they may be used in aqueous dispersions or latices, as both will diffuse into the organic polymer and be efficacious when the polymer is isolated by drying of the latex to form a film. The preferred isothiazolones and stabilizers of the present invention may also be used in oil or alkyl paint formulations.

It is known in the art that the performance of biocides can frequently be enhanced by combination with one or more other biocides. In fact, there have been numerous examples of synergistic combinations of biocides. Thus, other known biocides may be combined advantageously with the stabilized isothiazolones of this invention.

The isothiazolone and copper compound may be separately blended into the paint to be stabilized or, preferably, the isothiazolone and the copper compound, with or without organic solvent, may be precombined into a single package or solution before being added to the paint to be stabilized. The single package combination of isothiazolone, copper compound, and optional organic solvent offers the advantage of improved control of the ratio of isothiazolone to copper compound being added to the paint since a single operation is involved rather than the several steps involved when each ingredient is added separately. In addition, the paint formulator will require only one storage vessel for single-package formulations, rather than the several which would be required if each component were to be supplied separately. Also, a one-step operation is inherently simpler than the multistep process of adding each ingredient separately where the chance for spillage or error is increased.

The following examples illustrate a few embodiments of the present invention. All percentages are by weight unless otherwise specified.

EXAMPLES

1. Preparation of Copper Salts Useful in the Invention

A. Copper dioctyl sulfosuccinate

Into a fritted column was added: 12 g (12 meq H+) ion exchange resin (Amberlite ® IR 120 brand). Resin beads were washed with 100 ml deionized water. Into a 50 ml beaker were added: 7 g (10 meq) sodium dioctyl sulfosuccinate (Triton ® GR-5M brand), 7 g water, and 7 g isopropanol. The surfactant solution was run through the column and collected in a 100 ml beaker containing: 0.5 g (10 meq Cu) copper hydroxide and 20 g water. The effluent/copper hydroxide mixture was swirl mixed while collecting the effluent. A 10 g water rinse of the column was added to the copper mixture. Extraction of the beaker's contents was done with $2 \times 25$ ml toluene, the toluene solubles were dried with molecular sieve, rotary evaporator stripping removed the toluene, and the resulting solids were vacuum dried overnight at room temperature.

A blue-green semi-solid product was isolated. Recovery was near 100%. Elemental analysis (expect/found): C 53.0/50.4, H 8.2/9.5, Cu 7.0/7.3, S 7.1/6.0 and Cu/S 0.99/1.22.

B. Copper Dodecylbenzene sulfonate

Into a fritted column was added: 12 g (12 meq H+) ion exchange resin (Amberlite ® IR 120 brand). Resin beads were washed with 100 ml deionized water. Into a 50 ml beaker were added: 8.6 g (10 meq) sodium dodecyl benzene sulfonate (Biosoft D-40 brand), 7 g water, and 7 g isopropanol. The Biosoft D-40 solution was run through the column and collected in a 100 ml beaker containing: 0.58 g (12 meq Cu) copper hydroxide mixture and 20 g water. The effluent/copper hydroxide mixture was swirl mixed while collecting the effluent. A 10 g water rinse of the column was added to the copper mixture. Extraction of the beaker's contents was done with $2 \times 25$ ml toluene. The toluene solubles were dried with molecular sieve. Stripping, on a rotary evaporator removed the toluene, and the resulting solids were vacuum dried overnight at room temperature.

A blue-green waxy product was isolated. Recovery was near 100%. Elemental analysis (expect/found): C 61.0/53.4, H 8.2/9.2, Cu 8.9/7.7, S 9.0/7.5 and Cu/S 0.99/1.03.

C. Copper petroleum sulfonate

Into a fritted column was added: 12 g (12 meq H+) ion exchange resin (Amberlite ® IR 120 brand). Resin beads were washed with 100 ml deionized water. Into a 50 ml beaker were added: 10 g (10 meq) petroleum sulfonate (Petronate HL brand), 7 g water, and 7 g isopropanol. The Petronate HL solution was run through the column and collected in a 100 ml beaker containing: 0.5 g (10 meq Cu) copper hydroxide and 20 g water. The effluent/copper hydroxide mixture was swirl mixed while collecting the effluent. A 10 g water rinse of the column was added to the copper mixture. Extraction of the beaker's contents was done with 2×25 ml toluene, the toluene solubles were dried with molecular sieve, rotary evaporator stripping removed the toluene, and the resulting solids were vacuum dried overnight at room temperature.

A blue-green waxy product was isolated. Recovery was near 100%. Elemental analysis (expect/found): C 65.2/64.3, H 10.9/10.0, Cu 4.3/4.3, S 4.4/4.4 and Cu/S 0.98/0.99.

D. Copper dodecylbenze sulfonate from dodecylbenzene sulfonic acid (DBSA).

A 500 ml r.b. flask was fitted with a Barrett trap, water cooled condensor and magnetic stirrer. Into the flask 100 ml Solvesso 100, (CAS Number 64742-95-6) 120 g (0.36 moles) Naxel AAS-98S (98% Linear DBSA) and 25 g (0.26 moles) of copper hydroxide were added. The flask was heated to approximately 170° C. in an oil bath and the mixture was refluxed with stirring for 4½ hours. Six ml of water of neutralization was collected in the trap. The cooled solution was diluted with an additional 250 ml Solvesso 100 and filtered after standing. The brown solution contained 2.7% Cu as the dodecyl benzene sulfonate salt.

2. Preparation of Comparative Copper Salts Not Useful in the Invention (Comparative)

A. Alkyl naphthalene sulfonate

Into a fritted column were added: 12 g (12 meq H+) ion exchange resin (Amberlite ® IR 120 brand). Resin beads were washed with 100 ml deionized water. Into a 50 ml beaker were added: 3.8 g (10 meq) alkyl naphthalene sulfonate (Morewet B brand), 7 g water, and 7 g isopropanol. The Morewet B solution was run through the column and collected in a 100 ml beaker containing: 0.5 g (10 meq Cu) copper hydroxide and 25 g water. The effluent/copper hydroxide mixture was swirl mixed while collecting the effluent. A 10 g water rinse of the column was added to the copper mixture. Extraction of the beaker's contents was done with 2×25 ml toluene, the toluene solubles were dried with molecular sieve, rotary evaporator stripping removed the toluene. Essentially no material was recovered indicating the reaction product (if any) was not soluble in aromatic hydrocarbon or useful in the practice of this invention.

B. Linear alkene ("olefin") sulfonate

Into a fritted column were added: 12 g (12 meq H+) ion exchange resin (Amberlite ® IR 120 brand). Resin beads were washed with 100 ml deionized water. Into a 50 ml beaker were added: 7.5 g (10 meq) linear alkene sulfonate (Witconate AOS brand), 7 g water, and 7 g isopropanol. The Witconate AOS solution was run through the column and collected in a 100 ml beaker containing: 0.5 g (10 meq Cu) copper hydroxide and 25 g water. The effluent/copper hydroxide mixture was swirl mixed while collecting the effluent. A 10 g water rinse of the column was added to the copper mixture. Extraction of the beaker's contents was done with 2×25 ml toluene, the toluene solubles were dried with molecular sieve, rotary evaporator stripping removed the toluene. No material was recovered after the toluene was removed.

C. Alkyl taurate

Into a fritted column were added: 12 g (12 meq H+) ion exchange resin (Amberlite ® IR 120 brand). Resin beads were washed with 100 ml deionized water. Into a 50 ml beaker were added: 6.4 g (10 meq) sodium alkyl taurate (Igepon T-77 brand), 7 g water, and 7 g isopropanol. The Igepon T-77 solution was run through the column and collected in a 100 ml beaker containing: 0.5 g (10 meq Cu) copper hydroxide and 25 g water. The effluent/copper hydroxide mixture was swirl mixed while collecting the effluent. A 10 g water rinse of the column was added to the copper mixture. Extraction of the beaker's contents was done with 2×25 ml toluene, the toluene solubles were dried with molecular sieve, rotary evaporator stripping removed the toluene, and the resulting solids were vacuum dried overnight at room temperature.

A green blue solid product was isolated. Recovery was low (<10% of the calculated). Elemental analysis (expect/found): C 48/57.0, H 9.3/10.6, Cu 7.3/10.9, S 7.4/0.9 and Cu/S 0.99/12.0, indicating lack of sulfonic functionality.

3. Stabilization of 3-Isothiazolones with Copper Salts of the Invention

The solid test materials were each mixed with Aromatic 150 to prepare stabilizer solutions. The stabilizer solutions and 4,5-dichloro-2-n-octyl-3-isothiazolone (100% ai) were charged into AC-64 latex paint (formulation listed in Appendix) to give 27 ppm Cu and 900 ppm 4,5-dichloro-2-n-octyl-3-isothiazolone ai. These paints were heat aged at 60° C. and were sampled at 0 time, 5 days and 10 days. The sampled material was analyzed for ppm ai remaining. Results are listed in Table I.

TABLE I

Dichloro Octyl Isothiazolones + Copper Stabilizers
Heat Aged at 60° C.

| Stabilizer | Color | Charged Isothiazolone PPM | Charged Copper PPM | % Isothiazolone Remaining 0 Days | 5 Days | 10 Days |
|---|---|---|---|---|---|---|
| None (Control) | | 900 | 0 | 100 | 0 | 0 |
| Cu-Biosoft D-40 | Blue-Green | 900 | 27 | 100 | 100 | 20 |
| Cu-Triton GR-5M | Blue-Green | 900 | 27 | 100 | 100 | 100 |

TABLE I-continued

| | Dichloro Octyl Isothiazolones + Copper Stabilizers Heat Aged at 60° C. | | | | | |
|---|---|---|---|---|---|---|
| | | Charged | | % Isothiazolone Remaining | | |
| Stabilizer | Color | Isothiazolone PPM | Copper PPM | 0 Days | 5 Days | 10 Days |
| Cu-Petronate HL | Green-Blue | 900 | 27 | 100 | 100 | 100 |

Paint Compositions Comprising 3-Isothiazolone Stabilized with Copper Salts

| AC-64 LATEX PAINT FORMULATIONS | |
|---|---|
| Material | lb/50 gal |
| Natrosol 250 MHR | 1.5 |
| Ethylene glycol | 12.5 |
| | Premix |
| Water | 56.0 |
| Tamol 960 (40%) | 3.6 |
| KTPP | 0.75 |
| Triton CF-10 | 1.3 |
| Colloid 643 | 0.5 |
| Propylene glycol | 17.0 |
| Ti-Pure R-902 | 112.5 |
| Minex 4 | 79.7 |
| Icecap K | 25.0 |
| Attagel 50 | 2.5 |
| | Let Down |
| AC-64 (60.5%) | 153.0 |
| Colloid 643 | 1.5 |
| Texanol | 4.7 |
| Ammonia (28%) | 1.16 |
| Natrosol 250 MHR (2.5%) | 53.50 |
| Water | 54.46 |
| Total | 581.17 lb/50 gal |

I claim:

1. An isothiazolone concentrate composition comprising
a. an oil soluble, water insoluble 3-isothiazolone compound of the formula:

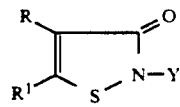

wherein Y is an unsubstituted alkyl group of 2 to 18 carbon atoms; a substituted alkyl group of 2 to 18 carbon atoms having at least one hydrogen atom replaced by hydroxy, halo, cyano, alkylamino, dialkylamino, phenylamino, halophenylamino, carboxy, carbalkoxy, alkoxy, aryloxy, morpholino, piperidino, pyrrolidonyl, carbamoxy, or isothiazolonyl, wherein the total number of carbon atoms in the substituted alkyl group does not exceed 18; an unsubstituted or halo-substituted alkenyl group of 4 to 18 carbon atoms; unsubstituted or halo-substituted alkynyl group of to 18 carbon atoms; an unsubstituted or alkyl-substituted cycloalkyl group having a four to six carbon atom ring and up to 12 carbon atoms; an unsubstituted or a halo-, lower alkyl-, or lower alkoxy-substituted aralkyl group wherein the total number of carbon atoms in the aralkyl group does not exceed 10; or an unsubstituted or a halo-, nitro-, lower alkyl-, or lower carbalkoxy-, substituted aryl group wherein the total number of carbon atoms in the aryl group does not exceed 10; and
R and $R^1$ are the same or different substituent selected from hydrogen, halogen, or a ($C_1$-$C_4$) alkyl group;
b. an amount sufficient to stabilize said 3-isothiazolone compound in a subsequent use dilution of a copper salt selected from the group consisting of copper dodecylbenzene sulfonate, copper dioctyl sulfosuccinate, and copper petroleum sulfonate and;
c. a sufficient amount of an organic solvent to dissolve said 3-isothiazolone and said copper salt.

2. Composition according to claim 1 wherein said 3-isothiazolone is selected from the group consisting of 2-n-octyl-3-isothiazolone, 4,5-dichloro-2-cyclohexyl-3-isothiazolone, and 4,5-dichloro-2-n-octyl-3-isothiazolone.

3. Composition according to claim 1 wherein said organic solvent is selected from the group consisting of xylene, naphtha, and psuedocumene.

4. Composition according to claim 1 which comprises from about 0.01 to about 50 parts of said isothiazolone (a); from about 0.0001 to about 10 parts of said copper compound (b), and which further comprises from about 40 to about 99.9899 parts of a solvent.

5. Composition according to claim 1 which comprises from 1 to 25 parts of (a), from 0.1 to 10 parts of (b) and from 65 to 98.9 parts of the solvent.

6. A coating or impregnant composition comprising from about 0.1 ppm to about 2 percent by weight of the composition of claim 1.

7. A marine antifoulant composition comprising about 1-10 percent by weight of the composition of claim 1.

8. Metal working fluid concentrate composition comprising a metal working fluid and about 0.1 ppm to about 2 percent by weight of a composition according to claim 1.

9. A metal working fluid use dilution composition comprising metal working fluid concentrate according to claim 8 and water.

10. A wood preservative composition comprising about 0.01 to 30% by weight concentration of a composition according to claim 1 dissolved in mineral spirits.

11. Composition comprising about 0.01 to 30% by weight concentration of a composition according to claim 1 in water and emulsifier.

12. Article comprising wood impregnated or preserved with a composition according to claim 10.

13. Article comprising wood impregnated or preserved with a composition according to claim 11.

* * * * *